United States Patent [19]

Ingendoh et al.

[11] Patent Number: 4,681,892
[45] Date of Patent: Jul. 21, 1987

[54] ISOXAZOLIDINE INSECTICIDES AND FUNGICIDES

[75] Inventors: Axel Ingendoh, Velbert; Wolfgang Scheinert, Leverkusen; Benedikt Becker, Mettmann; Kurt Halcour, Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 834,169

[22] Filed: Feb. 27, 1986

[30] Foreign Application Priority Data

Mar. 16, 1985 [DE] Fed. Rep. of Germany ....... 3509547

[51] Int. Cl.$^4$ ..................... A61K 31/42; C07D 261/02
[52] U.S. Cl. .................................... 514/378; 548/240
[58] Field of Search ................ 548/240, 206; 514/378

[56] References Cited

FOREIGN PATENT DOCUMENTS 2339185 2/1974 Fed. Rep. of Germany .
3418395 11/1985 Fed. Rep. of Germany ...... 548/240
7018294 6/1970 Japan .

OTHER PUBLICATIONS

Amadei-Sale, *The Chemical Abstracts*, vol. 80, 133415n.

*Primary Examiner*—Donald G. Daus
*Assistant Examiner*—Barbara Cassatt
*Attorney, Agent, or Firm*—Sprung, Horn, Kramer & Woods

[57] ABSTRACT

Insecticidally, arachnicidally and fungicidally active novel isoxazolidines of the formula

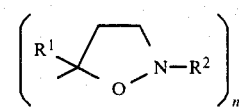

in which
  n is 2 or 3,
  $R^1$ is H or alkyl,
  $R^2$ is optionally substituted alkyl, cycloalkyl, alkenyl, alkinyl, aryl or a heterocyclic radical which is optionally substituted, and
  A is a di- or trivalent aryl or heteroaryl radical which is optionally substituted by alkyl, cycloalkyl, aralkyl, alkoxy, alkylthio, aryloxy, arylthio, halogen, CN, OH, halogenoalkyl, halogenoalkoxy, halogenoalkylthio, alkoxyalkyl, optionally halogen-substituted methylenedioxy or ethylenedioxy.

Some of the intermediates are also new.

10 Claims, No Drawings

ISOXAZOLIDINE INSECTICIDES AND FUNGICIDES

The present invention relates to new isoxazolidines, a process for their preparation, their use as pest-combating agents and new intermediate products for their preparation and a process for the preparation of these. Isoxazolidines have already been disclosed (J. Org. Chem. 44, 45 (1979) pages 835–839). However, nothing has been disclosed concerning biological properties and in particular concerning their suitability as pest-combating agents.

The new isoxazolidines of the formula I

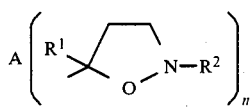

in which
n represents 2 or 3,
$R^1$ represents H or alkyl,
$R^2$ represents optionally substituted alkyl, cycloalkyl, alkenyl, alkinyl, aryl or represents saturated or unsaturated heterocyclic radicals which are optionally substituted, and
A represents di- or trivalent aryl or heteroaryl radicals which are optionally substituted by substituents from the series comprising alkyl, cycloalkyl, aryl, aralkyl, alkoxy, alkylthio, aryloxy, arylthio, halogen, CN, OH, halogenoalkyl, halogenoalkoxy, halogenoalkylthio, alkoxyalkyl, optionally halogen-substituted methylenedioxy and ethylenedioxy, have been found.

The new isoxazolidines of the formula I can occur in the form of their enantiomers or diastereomers and in the form of salts with inorganic or organic acids.

A process for the preparation of the new isoxazolidines of the formula I

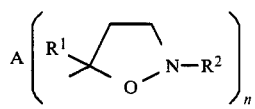

in which
n represents 2 or 3,
$R^1$ represents H or alkyl,
$R^2$ represents optionally substituted alkyl, cycloalkyl, alkenyl, alkinyl, aryl or represents saturated or unsaturated heterocyclic radicals which are optionally substituted, and
A represents divalent or trivalent aryl or heteroaryl radicals which are optionally substituted still further substituents from the series comprising alkyl, cycloalkyl, aryl, aralkyl, alkoxy, alkylthio, aryloxy, arylthio, halogen, CN, OH, halogenoalkyl, halogenoalkoxy, halogenoalkylthio, alkoxyalkyl, optionally halogen-substituted methylenedioxy or ethylenedioxy,
has been found, which is characterized in that hydroxylamines of the formula II

in which $R^2$ has the meaning given above, are reacted with formaldehyde and alkenes of the formula III

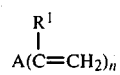

in which
A, $R^1$ and n have the meaning given above.

Some of the hydroxylamines of the formula II are new. The new alkyl-substituted cycloalkyllhydroxylamines of the formula IV

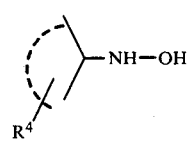

in which
$R^4$ represents alkyl, have been found.

The alkyl-substituted cycloalkylhydroxylamines of the formula IV are obtained by reducing alkyl-substituted cycloalkanone oximes of the formula V

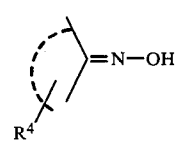

in which
$R^4$ represents alkyl.

Alkyl-substituted cycloalkanone oximes of the formula V are known or can be prepared analogously to known processes (Tetrahedron, 1967, 23(5)2421-9).

Some of the alkenes of the formula III are known or can be prepared analogously to known processes. 3,5-Diisopropenylcumene is new.

Such processes for the preparation of the alkenes of the general formula III are, for example, (a) Elimination of HX from compounds of the general formula VI

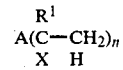

in which
A, $R^1$ and n have the meaning given in formula I and X represents hydrogen, halogen, hydroxyl, $OSO_2$—$R^3$ or $OCO$—$R^3$ ($R^3 = C_1$-$C_4$-alkyl), and (b) Elimination of HX from compounds of the general formula VII

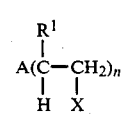

in which
A, $R^1$, n and X have the meaning given in formula VI, (c) Olefination (by the Wittig method) of compounds of the general formula VIII

VIII in which
A, $R^1$ and n have the meaning given in formula I, with ylides of the general formula IX $$W_3P=CH_2 \quad \text{IX}$$

in which
W represents, for example, phenyl.

Isoxazolidines of the formula I are suitable for combating pests, in particular for combating harmful mites and insects. The compounds also possess outstanding fungicidal actions. Since the known isoxazolidines were not known to possess any biological activity at all, it was surprising that the compounds according to the invention have such an excellent action as pest-combating agents and in particular as insecticides, acaricides and fungicides.

Preferred isoxazolidines according to the invention, of the formula I, are those in which
A represents aryl, in particular phenyl or naphthyl, which is optionally substituted by $C_{1-4}$-alkyl,
n represents 2 or 3,
$R^1$ represents hydrogen or $C_{1-4}$-alkyl, and
$R^2$ represents $C_{1-10}$-alkyl, $C_{3-6}$-cycloalkyl, $C_{2-4}$-alkenyl, $C_{2-4}$-alkinyl, phenyl or naphthyl or represents $C_{1-6}$-alkyl which is substituted by halogen, OH, CN, amino, $C_{1-4}$-alkylamino, $C_{1-4}$-dialkylamino, $C_{1-4}$-alkoxy, $C_{3-6}$-cycloalkyl, optionally substituted phenyl, naphthyl, phenoxy, phenylthio, hydroxycarbonyl-$C_{1-4}$-alkyl or (OCO-$C_{1-4}$-alkyl), or represents $C_{3-6}$-cycloalkyl which is substituted by $C_{1-6}$-alkyl, halogen or CN, or represents phenyl which is substituted by halogen, $NO_2$, CN, OH, amino, $C_{1-4}$-alkylamino, di-$C_{1-4}$-alkylamino, carbonyl-($C_{1-4}$-alkoxy) or (—$COOC_{1-4}$-alkyl), or represents optionally substituted phenoxy, naphthyloxy or biphenyloxy.

Very particularly preferred isoxazolidines of the formula I are those in which
A represents phenyl which is optionally substituted by $C_{1-4}$-alkyl, in particular isopropyl,
n represents 2 or 3,
$R^1$ represents hydrogen or methyl, and
$R^2$ represents $C_{1-6}$-alkyl, in particular methyl, ethyl, butyl, t-butyl, pentyl, pinacolyl or hexyl (and their isomers) which may optionally be substituted by cyclopropyl, or represents cyclohexyl which may optionally be substituted by $C_{1-6}$-alkyl.

Very particularly preferred compounds of the formula I are those in which $R^2$ represents alkyl having at least 4 C atoms, which may be optionally substituted by cyclopropyl, and represents cyclohexyl which is optionally substituted by branched $C_{4-6}$-alkyl.

The following compounds may be mentioned individually:

| n | A | $R^1$ | $R^2$ |
|---|---|---|---|
| 2(in the 2,5 position) | pyridyl | H | pinacolyl |
| 2(in the 1,7 position) | naphthyl | H |  |
| 2(in the 2,4 position) | thienyl | H | isopropyl |
| 2(in the 5,7 position) | quinolyl | $CH_3$ | 2-t-butyl-hexyl |
| 2(in the 1,3 position) | 5-bromo-phenyl | $CH_3$ | pinacolyl |

The compounds of the formula I can be in the form of their diasteromers and enantiomers, owing to the asymmetric C atoms denoted by A and B in the formula below:

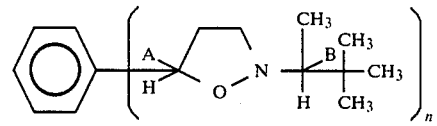

The componds of the formula I can occur in the form of their salts.

The following acids which can form salts with the isoxazolidines of the formula I may be preferably mentioned: HCl, $H_2SO_4$, $HSO_4^-$, $H_3PO_4$, $HPO_4^-$, $HCLO_4$, HBr, HI, HF, $HNO_3$, $H_2CO_3$, $HCO_3^-$, acetic acid, oxalic acid, malonic acid, succinic acid, malic acid, tartaric acid, maleic acid, fumaric acid, methanesulphonic acid, benzoic acid, substituted benzoic acids, formic acid, chloroacetic acid, toluenesulphonic acid, benzenesulphonic acid, trichloroacetic acid, fluoroacetic acid, phthalic acid, napthalenesulphonic acid and nicotinic acid.

The process for the preparation of the isoxazolidines of the formula I can be carried out in such a way that the hydroxylamines of the formula II, formaldehyde and the alkenes of the formula III are combined and reacted. It may be represented by the following equation:

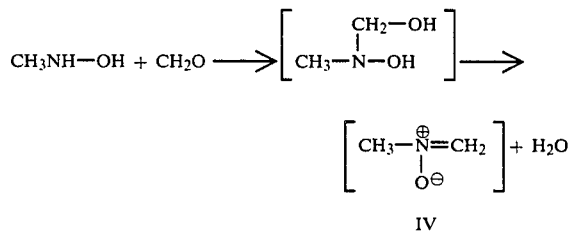

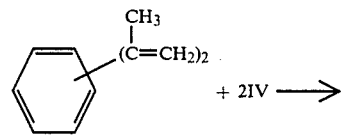

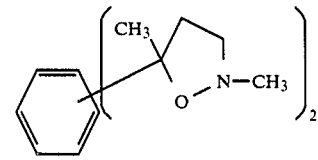

The hydroxylamines of the formula II which are employed for the preparation of the isoxazolidines of the formula I are known per se or can be prepared by processes which are known per se. In formula II, $R^2$ preferably has the preferred meanings stated for the compounds of the formula I.

The following hydroxylamines of the formula II may be particularly mentioned:

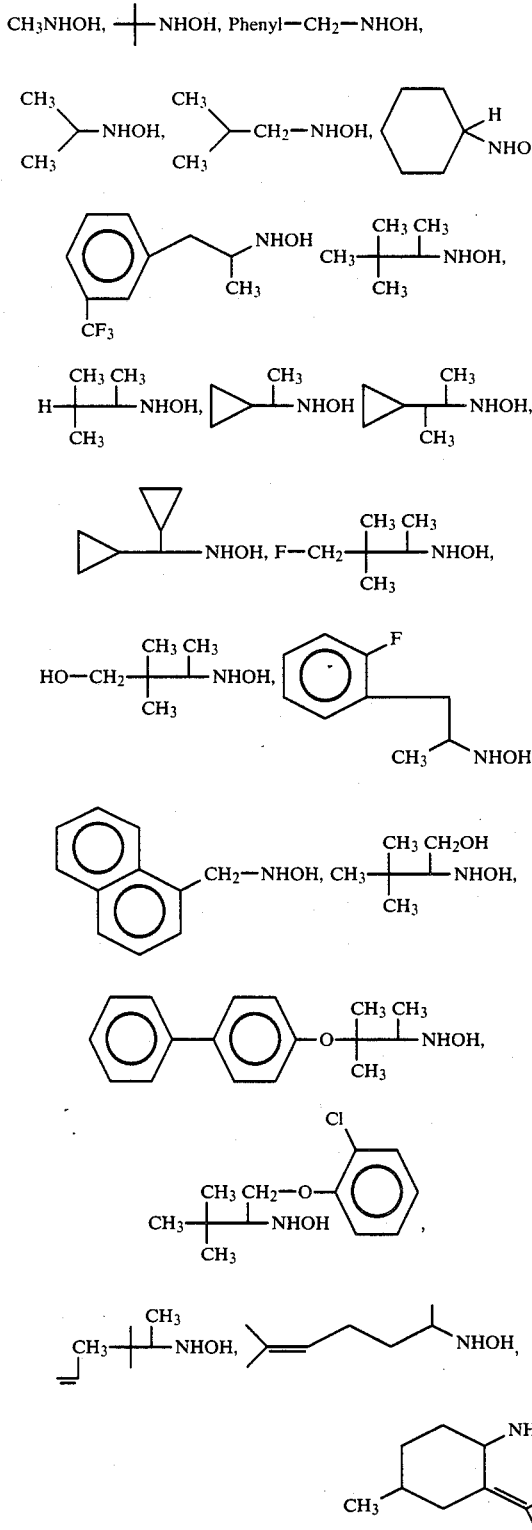

2-Tert.-butyl-cyclohexylhydroxylamine is likewise particularly preferred. It is new, and its preparation is described further below.

To prepare the isoxazolidines of the formula I, formaldehyde is employed in the form of formalin or paraformaldehyde or of compounds, such as trimethylene oxide, which eliminate formaldehyde.

To prepare the isoxazolidines of the formula I, alkenes of the formula III are used in which the radicals A and $R^1$ have the preferred and particularly preferred meanings stated for the compounds of the formula I. The alkenes of the formula III which are stated in the examples may be mentioned in particular.

The process for the preparation of the compounds according to the invention, of the formula 1, is carried out at temperatures of 0°–100° C., preferably at 100°–140° C.

1-2, preferably 1-1.5, equivalents of hydroxylamine of the formula II and 1-2.5, preferably 1-1.5, equivalents of formaldehyde are employed per olefinic double bond of the alkenes of the formula III.

The process is usually carried out under atmospheric pressure. It is preferably carried out in the presence of diluents. Suitable diluents are optionally substituted hydrocarbons, such as toluene, xylene, benzene, chloroform, alcohols, such as ethanol, or isopropanol, ethers, such as dialkyl ethers, esters, such as ethyl acetate, and tetrahydrofuran, acetonitrile, dimethylformamide and dimethyl sulphoxide.

It is also possible to add formaldehyde to the hydroxylamines of the formula II and then add the alkenes of the formula III to the reaction mixture.

In a particularly preferred procedure, it is also possible to react the hydroxylamines of the formula II in the form of their salts with inorganic acids, in particular HCl, and formaldehyde, preferably in the form of its aqueous formalin solution, and then to add the alkene of the formula III to the reaction solution.

The process is carried out at tempertures of 20°–150° C. under atmospheric pressure.

Formaldehyde can also be employed in excess (about 1–5 fold per double bond).

Suitable diluents which may be mentioned are inert organic diluents, such as alcohols, such as methanol, ethanol or isopropanol, hydrocarbons, such as toluene, and dimethylformamide, dimethyl sulphoxide and high-boiling ethers.

Strong inorganic bases which may be mentioned are alkali metal and alkaline earth metal hydroxides, such as sodium hydroxide solution or potassium hydroxide solution, and alkali metal and alkaline earth metal carbonates and bicarbonates.

The following may be mentioned as suitable organic bases: trimethylamine, triethylamine, N-ethyldiisopropylamine, N,N-dimethylaniline, N,N-diethylaniline, N,N,N',N'-tetra-methylethylenediamine, N,N,N',N'-tetraethylethylenediamine, lutidine, picoline and pyridine.

Neutralization is effected at about 20° C., to a pH value of 6–8.

The alkene of the formula III and a "water-entraining agent" are then added to the reaction mixture.

The following may be mentioned as water-entraining agents: aromatic hydrocarbons, such as, in particular, benzene, toluene and xylene, and halogenated hydrocarbons, such as chloroform and carbon tetrachloride.

Thereafter, the reaction mixture is heated to 110°–140° C. Alcohol and water are distilled off azeotropically with the aid of the water-entraining agent.

After the alcohol has been distilled off and the water has been removed from the reaction mixture by means of the water-entraining agent, the reaction is allowed to continue at 110°-140° C., and the mixture is then worked up in a customary manner.

As already mentioned, the hydroxylamines of the formula IV are new. The process for their preparation can be represented by the following equation for the case in which 4-methylcyclohexanone oxime and NaBH₃CN are used:

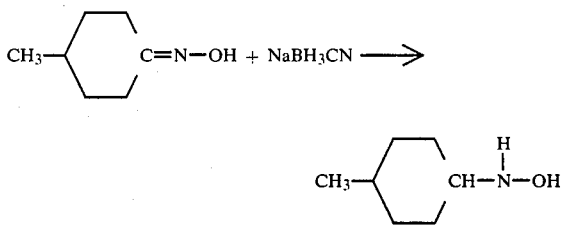

The new alkyl-substituted cycloalkylhydroxylamines of the formula IV in which the cycloalkyl ring contains 4–6 C atoms may be particularly preferably mentioned. Cyclobutane, cyclopentane and cyclohexane may be very particularly preferably mentioned as cycloalkyl rings. Cyclohexane may be particularly mentioned.

Alkyl radicals having 1–7 C atoms, in particular 3–5 C atoms, may be mentioned as substitutents of the cycloalkyl rings. Branched alkyl radicals having 3–5 C atoms, such as, for example t-butyl, may be particularly preferably mentioned as alkyl substituents. T-butyl-cyclohexanonehydroxylamine may be particularly mentioned.

The cycloalkanone oximes of the formula V which are employed for the preparation of the hydroxylamines of the formula IV are known or can be prepared analogously to known processes (Tetrahedron 1967, 23(5) pages 2421-9).

Preferably employed cycloalkanone oximes are those which lead to the abovementioned preferred cycloalkanonehydroxylamines.

Particularly suitable reducing agents are alkali metal cyanoborohydrides, such as sodium cyanoborohydride. However, the reduction may also be carried out using other suitable reducing agents.

The reduction of the cycloalkanone oximes with sodium cyanoborohydride is carried out at −20° C. to +100° C., preferably at about 20° C.

It is carried out under atmospheric pressure.

The starting components are employed in an approximately equimolar ratio:

Diluents are employed in the reaction. The following may be mentioned as diluents: alcohols, such as methanol, ethanol, isopropanol or ethylene glycol. It is also possible to carry out the reaction in aqueous alcohols.

A pH value of the reaction solution of about 1-4 is employed. The pH value can be determined by means of a calibrated glass electrode. Furthermore, the addition of a colour indicator, such as bromocresol green or methyl orange, is suitable for establishing the pH value.

Working-up can be effected in a manner which is known per se, by acidifying the mixture with a concentrated acid, such as hydrochloric acid, in order to decompose the cyanoborohydride and then rendering the mixture alkaline, and subsequently extracting the N-alkylhydroxylamine with organic solvents (see R. Borch J. Am. Chem. Soc. 93, 2897 (1971)).

However, after the end of the borohydride reduction and decomposition of the borohydride with a concentrated acid, such as hydrochloric acid, it is particularly advantageous to evaporate down the mixture in a vacuum from a water jet, and to extract the residue with chloroform or dichloromethane or alcohols, such as ethanol, isopropanol or methanol. The organic solution of the N-alkylhydroxylamine hydrochloride is dried with sodium sulphate or other suitable drying agents and evaporated down in a rotary evaporator.

The compounds of the formula IV may also be prepared in a manner which is known per se, by reduction of the corresponding nitro compounds with hydrogen, catalyzed by, for example, palladium on carbon (see U.S. Pat. No. 3,173,953) or by reduction with zinc dust in glacial acetic acid, with aluminum amalgam or with tin (II) chloride (see Houben Weyl Methoden der org. Chemie Volume 10/1 page 1153).

The particularly preferred alkenes of the general formula III which are employed as intermediate products and in which A represents phenyl, $R^1$ represents hydrogen or $C_1$–$C_3$-alkyl and n represents 2 or 3, can be prepared by, for example, catalytic dehydrogenation of compounds of the general formulae VI or VII (see above) in which X represents hydrogen.

The catalytic reaction can be carried out in a manner which is known per se, for example in the gas phase and at high temperatures (for example 400°–700° C.=673–973 K.) under atmospheric pressure or under elevated pressure, in the absence or presence of oxygen, oxygen-containing compounds, such as, for example, carbonyl sulphide, or other compounds which, like, for example, sulphur, are capable of dehydrogenating the compounds employed in the reaction by binding hydrogen. It is also possible to utilize the fact that the partial pressure of the organic compound employed can be reduced by adding steam, a procedure which is known per se and carried out industrially and by means of which the catalyst activity may be maintained over a longer period.

Examples of suitable catalysts for the catalytic dehydrogenation in the absence of oxygen, oxygen-containing compounds or compounds capable of effecting dehydrogenation by binding hydrogen, and under the stated pressure and temperature conditions, are commercial catalysts, for example those based on $Fe_2O_3$ or $Cr_2O_3$, which may furthermore contain other components, such as, for example, alkali metal carbonates and other metal oxides.

Similarly, dehydrogenation of the organic compound employed, in the gas phase at elevated temperatures (for example 300°–600° C.=573–873 K.) under atmospheric pressure or elevated pressure in the presence of oxygen, oxygen-containing compounds or compounds which are capable of effecting dehydrogenation by binding hydrogen, can be carried out using, for example, phosphate-containing catalysts, which are particularly suitable for this type of reaction.

These dehydrogenation reactions can be carried out in the customary industrial reactors which contain the catalyst in the form of a fixed bed, for example in tube reactors which are heated by flue gas or by a molten salt and permit more or less isothermal temperature control, or alternatively, for example, in adiabatic shelf-type reactors heated by flue gas. To achieve a particularly economical mode of operation, the liquid product mixture obtained can be recycled to the reactor together with the starting material after the desired end compounds have been separated off.

The active compounds are well tolerated by plants, have a favorable level of toxicity to warm-blooded animals, and are suitable for combating animal pests, especially insects, arachnida and nematodes, which are encountered in agriculture, in forestry, in the protection of stored products and of materials, and in the hygiene field. They are active against normally sensitive and resistant species and against all or some stages of development. The abovementioned pests include:

From the order of the Isopoda, for example, Oniscus asellus, Armadillidium vulgare and Porcellio scaber. From the order of the Diplopoda, for example, *Blaniulus guttulatus.* From the order of the Chilopoda, for example, *Geophilus carpophagus* and Scutigera spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp.. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp.. From the order of the Arachnida, for example, *Scorpio maurus* and *Latrodectus mactans.* From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The phytoparasitic nematodes include Pratylenchus spp., *Radopholus similis, Ditylenchus dipsaci, Tylenchulus semipenetrans,* Heterodera spp., Meloidoggne spp., Aphelenchoides spp., Longidorus spp., Xiphinema spp. and Trichodorus spp.

The active compounds are also suitable for combating fungal plant diseases, such as, for example, Pyrikularia oryzae in rice.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surfaceactive agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, oorn cobs and tobacco stalks; as emulsifying and/or foam-forming agents there are suitable: for example non-ionic and anionic emulsifiers, such as polyoxyethylene-fatty acid esters, polyoxyethylenefatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, and substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are also suitable for combating ectoparasites and endoparasites in the field of veterinary medicine.

The active compounds according to the invention are used in a known manner in the veterinary sector, such as by oral administration, for example in the form of tablets, capsules, drinks and granules, by dermal application, for example in the form of dipping, spraying, pouring on and spotting on, and dusting, and by parenteral administration, for example in the form of an injection.

EXAMPLE A

Test with *Lucilia cuprina* resistant larvae

Emulsifier:
 35 parts by weight of ethylene glycol monomethyl ether
 35 parts by weight of nonylphenol polyglycol ether To produce a suitable preparation of active compound, three parts by weight of active compound are mixed with seven parts by weight of the abovementioned mixture and the concentrate thus obtained is diluted with water to the particular desired concentration.

About 20 *Lucilia cuprina* res. larvae are introduced into a test tube which contains approx. 1 $cm^3$ of horse muscle and 0.5 ml of the preparation of active compound. After 24 hours, the degree of destruction is determined.

In this test, for example, the following compounds from the preparation examples show a superior activity compared to the prior art: 1, 3, 8 and 9.

EXAMPLE B

Test with Boophilus microplus resistant

Solvent:
 35 parts by weight of ethylene glycol monomethyl ether
 35 parts by weight of nonylphenol polyglycol ether To produce a suitable preparation of active compound, three parts by weight of active compound are mixed with seven parts by weight of the solvent mixture indicated above, and the concentrate thus obtained is diluted with water to the desired concentration.

10 adult *Boophilus microplus* res. are immersed for 1 minute in the active compound preparation to be tested. After transfer to plastic beakers and storage in a climatically controlled chamber, the degree of destruction is determined.

In this test, for example, the following compounds from the preparation examples show a superior activity compared to the prior art: 1, 3, 8 and 9.

EXAMPLE C

Laphygma Test

Solvent:
 7 parts by weight of dimethylformamide
Emulsifier:
 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the owlet moth (*Laphygma frugiperda*), as long as the leaves are still moist.

After the specified period of time, the destruction in % is determined. 100% means that all the caterpillars have been killed; 0% means that none of the caterpillars have been killed.

In this test, for example, the following compounds from the preparation examples show a superior activity compared to the prior art: 1, 3, 8 and 9.

EXAMPLE D

Tetranychus Test (Resistant)

Solvent:
7 parts by weight of dimethylformamide
Emulsifier:
1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with the common spider mite or two-spotted spider mite (*Tetranychus urticae*) in all stages of development are treated by being dipped into the preparation of the active compound of the desired concentration.

After the specified period of time, the destruction in % is determined. 100% means that all the spider mites have been killed; 0% means that none of the spider mites have been killed.

In this test, for example, the following compounds from the preparation examples show a superior activity compared to the prior art: 1, 3, 8 and 9.

PREPARATION EXAMPLES

General method

A solution of 0.1 mol of the bis- or trisalkene of the formula II in 250 ml of toluene is heated to 100° C., and an alcoholic aqueous solution obtained by adding 0.22 mol of an aqueous formalin solution (33% strength) to 0.22 mol of N-alkylhydroxylamine hydrochloride of the general formula III, neutralizing the mixture with potassium hydroxide solution (1 molar) in methanol and filtering off the solution from the potassium chloride is added.

First, methanol distills off, after which the mixture is heated to an external temperature of 140° C. During this procedure, toluene and water distil off azeotropically. The mixture is boiled under reflux for a further 5 hours. It is allowed to cool, solid residues are filtered off, and 100 ml of 10% aqueous hydrochloric acid are added. The aqueous phase is separated from the toluene and extracted twice with ether. The aqueous phase is rendered alkaline and extracted three times more with ether. The combined ether extracts are dried over sodium sulphate, the ether is distilled off and the residue is distilled in a high vacuum or purified by column chromatography.

The compounds of the table below were obtained by this method:

TABLE 3

| Example no. | Formula | Physical properties, data of the $^1$H—NMR spectrum CCDL$_3$,/ppm |
|---|---|---|
| 1 | (structure, o:m:p = 0:3:1) | 7.44–7.2 [m]<br>4.92 [n]<br>3.1–2.0 [m]<br>1.0 [1] |

Preparation examples

| | | |
|---|---|---|
| 2 | (structure, o:m:p = 0:3:1) | 7.50–7.20 [m]<br>4.95 [t]<br>2.0–1.0 [m]<br>1.0 [s] |
| 3 | (structure, o:m:p = 0:3:1) | 7.4–7.0 [m]<br>4.95 [b]<br>3.0–2.0 [m]<br>1.0–0.8 [3 × 5] |
| 4 | (structure, o:m:p = 0:3:1) | 7.4–7.15 [m]<br>4.95 [b]<br>1.05 [s] |

TABLE 3-continued

| Example no. | Formula | Physical properties, data of the $^1$H—NMR spectrum CCDL$_3$,/ppm |
|---|---|---|
| 5 | 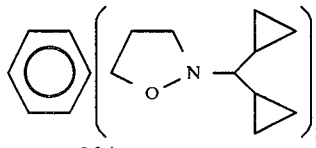 o:m:p = 0:3:1 | 7.45-7.2 [m]<br>5.00 [t]<br>0.7-0.25 [m] |
| 6 | 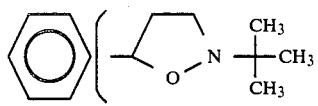 o:m:p = 0:3:1 | 7.4-7.2 [m]<br>4.95 [t]<br>11.08 [s] |
| 7 | 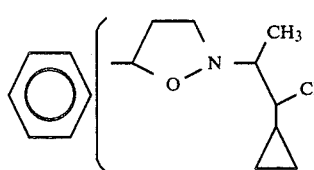 o:m:p = 0:3:1 | 7.45-7.2 [m]<br>5.00 [t]<br>1.9-0.9 [m]<br>0.1-0.5 [m] |
| 8 | 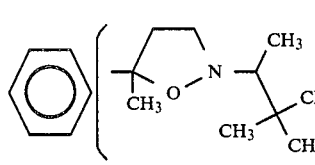 in 1,3-position | 7.60-7.20 [m]<br>1.45 [s]<br>1.55 [s]<br>0.90 [s] |
| 9 | 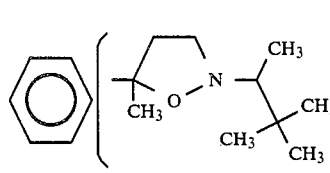 in 1,4 position | 7.45-7.20 [m]<br>3.0-2.0 [m]<br>1.55 [s]<br>1.50 [s]<br>1.01 [s]<br>1.08 [s] |
| 10 | 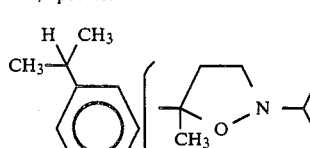 in 3,5-position | 7.30-7.20 [m]<br>3.0-2.0 [m]<br>1.5 [s]<br>1.23 [s]<br>1.52 [s]<br>1.00 [s]<br>1.26 [s] |
| 11 | 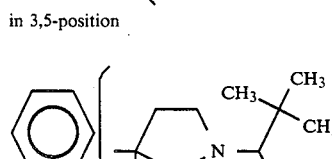 | 7.60-7.30 [m]<br>3.0-2.0 [m]<br>1.57 [s]<br>1.52 [s]<br>1.01 [s]<br>1.00 [s]<br>0.85 [s] |

PREPARATION OF THE STARTING MATERIALS

Example a

The following method was used for the preparation of di- and trivinylbenzenes:

An electrically heated tube reactor provided with a pre-evaporator is used. The reaction tube, having an internal diameter of 20 mm and a length of 400 mm, is heated electrically over a length of about 350 mm. The reactor is connected, via a short flanged connector, to a heated tube which is arranged above it, has an identical structure and the same dimensions and serves as a preevaporator. The feed points for water and the hydrocarbon mixture to be dehydrogenated are at the entrance of the pre-evaporator, the water and the hydrocarbon mixture to be dehydrogenated being fed separately to the apparatus by means of a reciprocating metering pump (Telab pump). The reactor charge consists of 100 ml of a commercial dehydrogenation catalyst (Girdler - Sudchemie G 64 C containing Fe$_2$O$_3$ as the main component, extrudates of 2 mm diameter), which is covered with a layer comprising 25 ml of Berl saddles in order to ensure that the hydrocarbon/steam mixture entering the reactor is better distributed over the tube cross section. The pre-evaporator contains a charge of 125 ml of Berl saddles. Perforated trays mounted at the bottom of the particular apparatus serve to hold the reactor and pre-evaporator charges.

The electric heaters of the pre-evaporator and reactor are set so that the hydrocarbon/steam mixture enters the reactor at a temperature of about 500° C. (=773 K.) and a maximum temperature of about 630° C. (=903 K.) is measured in the catalyst bed. The components of the reaction mixture which leave the reactor are collected in a round-bottomed flask provided with a cooling jacket containing water, and are condensed. The round-bottomed flask is provided with an outlet in the base to allow removal of the product. To recover any uncondensed components as completely as possible, a reflux condenser is connected in the path of the exit gas, downstream of the round-bottomed flask.

To carry out the dehydrogenation experiment, the preevaporator and the reactor are first heated so that a temperature of about 630° C. (=903 K.) is measured in the region of the reactor center, and a temperature of about 500° C. (=773 K.) is measured in the preevaporator. After a flow of water of about 180 ml/h has been set by means of the steam-metering pump, the heat outputs of the pre-evaporator and reactor are corrected so that the abovementioned temperatures are reached again. A flow of hydrocarbon of about 30 ml/h is then set by means of the hydrocarbon-metering pump. The condensate which has settled out in the separator is discharged at intervals of about 2 hours, and the hydrocarbon phase is separated off and, after 0.5% by weight of tert.butyl-pyrocatechol has been added as a polymerization inhibitor, is fed to the working up stage (see below).

With diethylbenzene as the main component of the hydrocarbon starting mixture (Experiment 1), several test runs based on this method and lasting about 300 hours each without interruption of the water and hydrocarbon feeds were carried out without any significant decrease in the catalyst activity. Before each of these test runs, fresh catalyst was employed. In contrast to this, in the case of the other substrates (Experiments 2 to 4) a mode of operation involving intermittent introduction of the hydrocarbon starting mixture was chosen, in which the hydrocarbon stream is switched off after the hydrocarbon has been fed in for a period of 6 hours, whereas the water feed continues uninterrupted.

After only water has been fed in for 6 hours, while the temperature in the middle of the reactor increases to about 650° C. (=923 K.), the hydrocarbon feed is begun again, a maximum temperature of 630° C. (=903 K.) being established again in the catalyst bed. Using this mode of operation, Experiments 2 to 4 were each extended over about 100 hours without any noticeable decrease in the catalyst activity being observed.

In all experiments, working up was carried out by fractional distillation in vacuo, the fractions which are shown in Table 2 and which contained the desired di- or trivinylbenzenes being obtained.

The results of the dehydrogenation experiments are summarized in the table.

TABLE 1

Results of the dehydrogenation experiments

| Experiment No. | Main component of the aromatic hydrocarbon mixture used for the dehydrogenation | | Composition of the liquid hydrocarbon mixture after the dehydrogenation | | | | | | | | |
|---|---|---|---|---|---|---|---|---|---|---|---|
| | Formula | % by weight | (1) Formula | % by weight | (2) formula | % by weight | (3) Formula | % by weight | (4) Formula | % by weight | (5) Formula | % by weight |
| a1 | diethylbenzene (o:m:p = 0.2:3:1) | 85 | diethylbenzene | 21.0 | ethylvinylbenzene | 18.5 | divinylbenzene | 38.0 | — | — | unidentified compounds | 22.5 |
| a2 | diisopropylbenzene (m-) | 98.2 | diisopropylbenzene | 15.0 | isopropenyl-isopropylbenzene | 20.5 | diisopropenylbenzene | 56.1 | — | — | unidentified compounds | 8.4 |
| a3 | diisopropylbenzene (p-) | 97.6 | diisopropylbenzene | 17.7 | isopropenyl-isopropylbenzene | 18.0 | diisopropenylbenzene | 58.4 | — | — | unidentified compounds | 6.0 |
| a4 | triisopropylbenzene | 96.0 | triisopropylbenzene | 20.5 | isopropenyl-diisopropylbenzene | 57.1 | diisopropenyl-isopropylbenzene | 9.4 | | 3.0 | unidentified compounds | 10.0 |

TABLE 2

Results from working up the reaction mixtures of experiments 1-4 by fractional vacuum distillation.

| Compound No. | Main component of the fraction used for further reaction Formula | % by weight | Fraction obtained from Experiment No. |
|---|---|---|---|
| b | 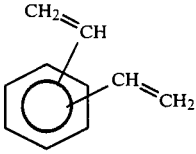 (o:m:p = 0:3:1) | 80 | 1 |
| c | 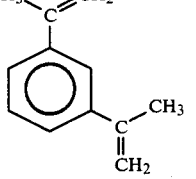 | 80 | 2 |
| d | 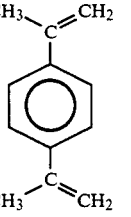 | 85 | 3 |
| e | 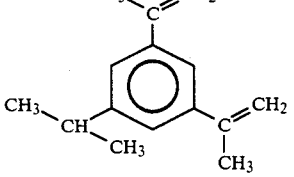 | 78 | 4 |
| f | 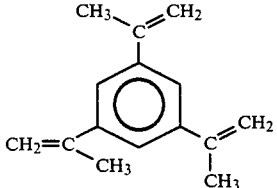 | 78 | 4 |

It will be understood that the specification and examples are illustrative but not limitative of the present invention and that other embodiments within the spirit and scope of the invention will suggest themselves to those skilled in the art.

We claim:

1. An isoxazolidine of the formula

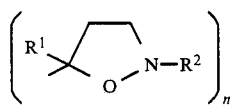 A in which
n is 2 or 3,
$R^1$ is H or $C_{1-4}$-alkyl,
$R^2$ is $C_{1-10}$-alkyl, optionally substituted by $C_{3-6}$-cycloalkyl; or is $C_{3-6}$-cycloalkyl, optionally substituted by $C_{1-10}$-alkyl or $C_{3-6}$-cycloalkyl,
A is a di- or trivalent phenyl radical which is optionally substituted by $C_{1-4}$-alkyl.

2. An isoxazolidine according to claim 1, in which
$R^1$ is hydrogen or $C_{1-4}$-alkyl, and
$R_2$ is $C_{1-10}$-alkyl, $C_{3-6}$-cycloalkyl, $C_{1-6}$alkyl which is substituted by $C_{3-6}$-cycloalkyl, or is $C_{3-6}$-cycloalkyl which is substituted by $C_{1-6}$-alkyl.

3. An isoxazolidine according to claim 1, in which
$R^1$ is hydrogen or methyl, and
$R^2$ is $C_{1-6}$-alkyl optionally substituted by cyclopropyl, or cyclohexyl optionally substituted by $C_{1-6}$-alkyl.

4. A compound according to claim 1, wherein such compound is bis-[2-(1,2,2-trimethylpropyl)-isoxazolidine-5-yl]-benzene of the formula

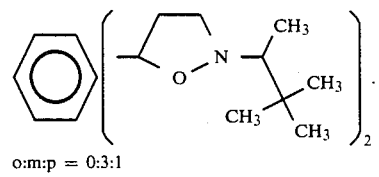

o:m:p = 0:3:1

5. A compound according to claim 1, wherein such compound is bis-[2-(1,2-dimethylpropyl)-isoxazolidin-5-yl]-benzene of the formula

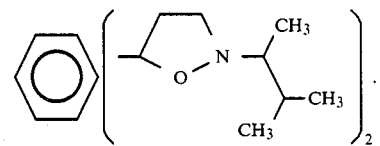

6. A compound according to claim 1, wherein such compound is 1,3-bis-[5-methyl-2-(1,2,2-trimethylpropyl)-isoxazolidin-5-yl]-benzene of the formula

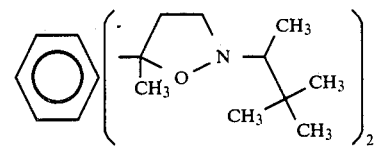

in 1,3-position

7. A compound according to claim 1, wherein such compound is 1,4-bis-[5-methyl-2-(1,2,2-trimethylpropyl)-isoxazolidin-5-yl]-benzene of the formula

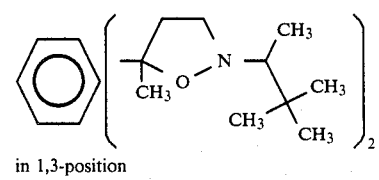

in 1,3-position

8. An insecticidal, arachnicidal or fungicidal composition comprising an insecticidally, arachnicidally or fungicidally effective amount of a compound according to claim 1 in admixture with a diluent.

9. A method of combating insects, arachnids or fungi which comprises applying thereto or to a habitat thereof an insecticidally, arachnicidally or fungicidally effective amount of a compound according to claim 1.

10. The method according to claim 9, wherein such compound is bis-[2-(1,2,2-trimethylpropyl)-isoxazolidine-5-yl]-benzene,
bis-[2-(1,2-dimethylpropyl)-isoxazolidin-5-yl]-benzene,
1,3-bis-[5-methyl-2-(1,2,2-trimethylpropyl)-isoxazolidin-5-yl]-benzene or
1,4-bis-[5-methyl-2-(1,2,2-trimethylpropyl)-isoxazolidin-5-yl]-benzene.

* * * * *

UNITED STATES PATENT AND TRADEMARK OFFICE
CERTIFICATE OF CORRECTION

PATENT NO. : 4,681,892
DATED : July 21, 1987
INVENTOR(S) : Axel Ingendoh, et al.

It is certified that error appears in the above-identified patent and that said Letters Patent is hereby corrected as shown below:

| | |
|---|---|
| Title Page, "Abstract", line 3 and Col. 21, line 60 | Delete "A" on right side of formula and insert --A-- in front of formula |
| Col. 4, line 23 | Delete "$HCLO_4$" and substitute --$HClO_4$-- |
| Col. 11, line 10 | Delete "born" and substitute --corn-- |
| Col. 15, Table 3, last line under last column | Delete "0.85[s]" and substitute --0.95[s]-- |
| Col. 22, line 39 | Insert --o:m:p=0:3:1-- |

Signed and Sealed this

Tenth Day of May, 1988

Attest:

DONALD J. QUIGG

Attesting Officer

Commissioner of Patents and Trademarks